United States Patent
Bastian et al.

(12) 
(10) Patent No.: US 6,551,780 B1
(45) Date of Patent: Apr. 22, 2003

(54) DETECTION OF GENE MUTATIONS OR AMPLIFICATIONS IN MELANOCYTIC NEOPLASMS

(75) Inventors: Boris Bastian, San Francisco, CA (US); Daniel Pinkel, Walnut Creek, CA (US)

(73) Assignee: The Regents of University of California, Oakland, CA (US)

( * ) Notice: Subject to any disclaimer, the term of this patent is extended or adjusted under 35 U.S.C. 154(b) by 0 days.

(21) Appl. No.: 09/541,364

(22) Filed: Mar. 31, 2000

(51) Int. Cl.$^7$ ............................ C07H 21/04; C12Q 1/68
(52) U.S. Cl. ............................ 435/6; 435/91.2; 536/23.1
(58) Field of Search .................... 435/6, 91.2; 536/23.1

(56) References Cited

U.S. PATENT DOCUMENTS 5,320,947 A * 6/1994 Cheever et al. ............... 435/29
6,261,775 B1 * 7/2001 Bastian et al. .................. 435/6

OTHER PUBLICATIONS

Barbacid, Ann. Rev. Biochem. vol. 56, pp. 779–827, 1987.*
Pierceall et al. "Ras Gene Mutation and Amplification in Human Non–Melanoma skin cancers" Molecular Carcinogenesis, vol. 4, pp. 196–202, 1991.*
Bos, "ras Oncogenes in Human Cancer: A review" Cancer Research vol. 49, pp. 4682–4689, Sep. 1989.*
Bastian et al. "Molecular cytogenetic analysis of spitz nevi shows clear differences in melanoma" J. of Invet. Dermatology, vol. 113, No. 6, pp. 1065–1069, Dec. 1999.*
Bastian et al., Cancer Research (1998) 58: 2170–2175.
Healy et al., Cancer Research (1996) 56: 589–593.
Lichter et al., Hum. Genet. (1988) 80: 224–234.
Matson et al., Analytical Biochemistry (1995) 224: 110–116.
Thompson et al., Cancer Genet. Cytogenet. (1995) 83: 93–104.
Wang et al., Jpn. J. Human Genet. (1995) 40: 243–252.
Wettengel et al., Int. J. of Oncology (1999) 14: 1177–1183.
Winokur et al. J. Cutan Pathol. (1990) 17: 342–347.
Pelling et al. "Role of the Ha–ras oncogene in skin cancer" Skin Cancer, p. 283–91, 1995.*
Ball et al. "RAS mutations in human melanoma" J. of Invetigative Dermatology, vol. 102, No. 3, pp. 285–290, Mar. 1994.*
Wilke et al. "H–Ras–1 gene mutations in basal cell carcinoma" Modern Pathology, vol. 6, No. 1, pp. 15–19, Jan. 1993.*
Jafari et al. "Analysis of ras mutation in human melanocytic lesions" J. Cancer Re. Clin. Oncol. vol. 121, pp. 23–30, 1995.*
Pelisson et al. "Low incidence of c–Ha–ras gene mutation in benign an dmalignant cutaneous lesions from transplant recipients" Int. J. Cancer, vol. 55, pp. 915–920, 1993.*

* cited by examiner

Primary Examiner—W. Gary Jones
Assistant Examiner—Jeanine Goldberg
(74) Attorney, Agent, or Firm—Townsend and Townsend and Crew LLP

(57) ABSTRACT

The present invention provides for methods of typing a melanocytic neoplasm, in particular for classifying a Spitz nevus. The methods comprise detecting in a tumor sample the presence of an increase in copy number of the whole chromosome 11p arm, particularly the presence of an 11p isochromosome, which is associated with the presence of a Spitz nevus. The invention further provides methods of typing a melanocytic neoplasm by detecting the presence of a mutated H-RAS gene, which is also associated with the presence of a Spitz nevus.

16 Claims, 1 Drawing Sheet

DETECTION OF GENE MUTATIONS OR AMPLIFICATIONS IN MELANOCYTIC NEOPLASMS

BACKGROUND OF THE INVENTION

The melanocyte can give rise to a number of morphologically different tumors. Most of them are biologically benign and are referred to as melanocytic nevi. Examples of melanocytic nevi are congenital nevi, Spitz nevi (including pigmented spindle cell nevi, which are regarded as a subtype of Spitz nevi), dysplastic or Clark's nevi, blue nevi, lentigo simplex, and deep penetrating nevus.

Spitz nevi are benign melanocytic neoplasms that can have considerable histological resemblance to melanoma. They were first described as "juvenile melanoma" by Sophie Spitz in 1948 and initially regarded as a subset of childhood melanoma that follows a benign course (Spitz, S., Am. J. Pathol. 24, 591–609 (1948)). Spitz nevi are common and account for about 1% of surgically removed nevi (Casso et al., J Am Acad Dermatol., 27, 901–13 (1992)). Although in general the pathological diagnosis of Spitz nevus is straightforward, there is a subset of cases in which it is difficult to impossible to histologically differentiate Spitz nevi from melanoma because of overlapping histological features, such as the presence of melanocytes with abundant cytoplasm and/or melanocytes with large pleomorphic nuclei. Additionally, mitotic figures, sometimes numerous, occur in both neoplasms.

Melanoma refers to malignant neoplasms of melanocytes. Accurate diagnosis and early treatment is of great importance because, although advanced melanoma has a poor prognosis, most melanomas are curable if excised in their early stages. Although in general the histopathological diagnosis of melanoma is straightforward, there is a subset of cases in that it is difficult to differentiate melanomas from benign neoplasm of melanocytes (LeBoit, P. E. SIMLULANTS OF MALIGNANT MELANOMA: A ROGUE'S GALLERY OF MELANOCYTIC AND NON-MELANOCYTIC IMPOSTERS, In Malignant Melanoma and Melanocytic Neoplasms, P. E. Leboit, ed. (Philadelphia: Hanley & Belfus), pp. 195–258 (1994)). Even though the diagnostic criteria for separating the many simulators of melanoma are constantly refined, a fraction of cases remains where an unambiguous diagnosis cannot be reached (Farmer et al., DISCORDANCE IN THE HISTOPATHOLOGIC DIAGNOSIS OF MELANOMA AND MELANOCYTIC NEVI BETWEEN EXPERT PATHOLOGISTS, Human Pathol. 27: 528–31 (1996)). The most frequent and important diagnostic dilemma is the differential diagnosis between Spitz nevus and melanoma.

Misdiagnosis of Spitz nevus as melanoma and vice versa has been repeatedly reported in the literature (Goldes et al., Pediatr. Dermatol., 1: 295–8 (1984); Okun, M. R. Arch. Dermatol. 115: 1416–1420 (1979); Peters et al., Histopathology, 10, 1289–1302 (1986)). A retrospective study of 102 melanomas of childhood found that only 60 cases were classified as melanoma by a panel of experts, the majority of the remainder being classified as Spitz nevi (Spatz, S., Int. J. Cancer 68, 317–24 (1996)). The presence of this diagnostic gray zone has even led the authors of a review article in the "Continuing Medical Education" section of the Journal of the American Association of Dermatology to conclude that Spitz nevus and melanoma may "actually exist on a continuum of disease" (Casso et al., J. Am. Acad. Dermatol., 27, 901–13 (1992)). The authors recommended that "treatment include complete excision of all Spitz nevi followed by reexcision of positive margins if present." The need for improved diagnostics for melanocytic neoplasms has led to numerous attempts to improve diagnostic accuracy by the use of markers that could be detected by immuno-histochemistry. While there have been prior efforts aimed at resolving this problem, none have been satisfactory. For example, even though tests employing markers such as S100, HMB45 are useful in establishing that a poorly differentiated tumor is of melanocytic lineage, adjunctive techniques have been of little help in separating benign from malignant melanocytic lesions.

Thus, there exists a great need for improved and accurate diagnostic methods to distinguish Spitz nevi from malignant melanoma. Furthermore, there is a need to distinguish melanocytic neoplasms that fall between Spitz nevi and malignant and are difficult to classify. The present invention addresses these and other needs by providing methods of typing a melanocytic neoplasm by detecting in a tumor sample the presence of an increase in copy number of an 11 p chromosome arm, particularly, detecting the presence of an 11p isochromosome, which indicates the presence of a Spitz nevus. Typing can also be performed by determining the presence of a mutated H-RAS gene, which is also associated with, or indicates the presence of a Spitz nevus.

SUMMARY OF THE INVENTION

The present invention provides for methods of typing a melanocytic neoplasm by detecting the presence of a mutated H-RAS gene in a patient sample, whereby the presence of the mutation in the H-RAS gene indicates the presence of a Spitz nevus, or classification as a Spitz nevus. Frequently, the mutation in the H-RAS gene is at codon 12, 13, or 61.

Typically, the copy number of the entire chromosome 11p including the H-RAS gene is increased relative to normal in the patient sample. The increase in gene copy number is frequently due to the presence of an 11p isochromosome.

In one embodiment of the invention, the presence of a mutation in the H-RAS gene is detected by amplifying a nucleic acid that encodes H-RAS or a fragment, and sequencing the amplified product to determine whether the sequence contains a mutation relative to a normal H-RAS sequence. Amplification is typically performed using PCR. Primers for the PCR reaction include those set out in SEQ ID NOs: 1 and 2, and SEQ ID NOs: 3 and 4. The nucleic acid that is amplified can be genomic DNA or RNA.

In another aspect of the invention, the presence of a mutation in the H-RAS gene is detected by contacting a nucleic acid from a skin tumor sample with a probe that selectively hybridizes to a target nucleic acid comprising an H-RAS gene to form a stable hybridization complex. The probe is contacted under condition in which the probe binds selectively to the target nucleic acid that includes the H-RAS gene. In one embodiment, the probe binds selectively to a mutated H-RAS gene. The method can further include a step of amplifying the nucleic acid from the sample. Preferably, the amplifying step is a PCR reaction, which can be performed, e.g., using oligonucleotides as set out in SEQ ID NOs: 1 and 2, and 3 and 4. The nucleic acid from the sample is preferably genomic DNA or RNA.

The invention also includes a method of detecting the presence of a mutated H-RAS gene by detecting a polypeptide encoded by the mutant H-RAS gene. Preferably the amount of polypeptide is quantified using an immunoassay, e.g., ELISA. In one embodiment, the polypeptide is detected using an antibody that selectively binds to the polypeptide encoded by the mutant H-RAS gene.

The methods of the invention further include a method of typing a patient melanocytic neoplasm from a patient by detecting the presence of an increase in copy number of the 11p chromosome arm whereby the presence of the increase in copy number of the 11p arm is indicates the presence of a Spitz nevus, or diagnosis of Spitz nevus. Typically, the methods comprise detecting the presence of an 11p isochromosome in a sample from a patient.

In one embodiment, the 11p isochromosome is detected by hybridizing a nucleic acid from the skin tumor sample with a probe that selectively hybridizes to sequences on chromosome 11p that are adjacent to the centromere and detecting the presence of one or more pairs of hybridization signals compared to normal. Additionally, the method can include hybridization of the nucleic acid sample with a second probe that is labeled with a second label distinguishable from the first and selectively hybridizes to a target nucleic acid sequence at chromosome 11q adjacent to the centromere; and detecting the presence of at least one pair of hybridization signals that consists of a signal from each of the probes. The probes are often labeled with fluorescent labels of different colors.

DEFINITIONS

To facilitate understanding the invention, a number of terms are defined below.

The terms "melanoma" or "cutaneous melanoma" refer to malignant neoplasms of melanocytes, which are pigment cells present normally in the epidermis and sometimes in the dermis. There are four types of cutaneous melanoma: lentigo maligna melanoma, superficial spreading melanoma (SSM), nodular melanoma, and acral lentiginous melanoma (AM). Melanoma usually starts as a proliferation of single melanocytes at the junction of the epidermis and the dermis. The cells first grow in a horizontal manner and settle an area of the skin that can vary from a few millimeters to several centimeters. As noted above, in most instances the transformed melanocytes produce increased amounts of pigment so that the area involved can easily be seen by the clinician.

The term "melanocytic neoplasm" refers to an accumulation of melanocytes that can undergo a benign, locally aggressive, or malignant course. "Melanocytic neoplasm" encompasses both benign melanocytic neoplasms, "nevi", and malignant melanocytic neoplasms, "melanoma".

The terms "Spitz nevi" or "Spitz nevus" refer to melanocytic neoplasms that can have considerable histological resemblance to melanoma. They generally are benign, but can recur locally, or rarely, spread to the lymph nodes. They were first described as "juvenile melanoma" and initially were thought of as a subset of childhood melanoma that follows a benign course. Spitz nevi are common and account for about 1% of surgically removed nevi.

The terms "tumor" or "cancer" in an animal refers to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumor, but such cells may exist alone within an animal. "Tumor" includes both benign and malignant neoplasms.

The phrase "typing" or "detecting" a neoplasm refers to the determination whether the neoplasm is, or has a high probability of being, a certain class of neoplasm. Classification can be based on whether the neoplasm is benign or malignant, or type of nevus, e.g., Spitz nevus. "Typing" or "detecting" can also refer to obtaining indirect evidence regarding the likelihood of the presence of a Spitz nevus or melanoma in the patient. Detection of a Spitz nevus versus a melanoma can be accomplished using the methods of this invention alone, or in combination with other methods or in light of other information regarding the state of health of the patient.

The terms "hybridizing specifically to", "specific hybridization", and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I*, Ch. 2, "Overview of principles of hybridization and the strategy of nucleic acid probe assays," Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1–3, Cold Spring Harbor Laboratory, Cold Spring Harbor Press, N.Y., and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

The term "labeled with a detectable label", as used herein, refers to a nucleic acid attached to a detectable composition, i.e., a label. The detection can be by, e.g., spectroscopic, photochemical, biochemical, immunochemical, physical or chemical means. For example, useful labels include $^{32}P$, $^{35}S$, $^{3}H$, $^{14}C$, $^{125}I$, $^{131}I$; fluorescent dyes (e.g., FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g. Dynabeads™), biotin, digoxigenin, or haptens and proteins for which antisera or monoclonal antibodies are available. The label can be directly incorporated into the nucleic acid, peptide or other target compound to be detected, or it can be attached to a probe or antibody that hybridizes or binds to the target. Label can be attached by spacer arms of various lengths to reduce potential steric hindrance or impact on other useful or desired properties. See, e.g., Mansfield, *Mol Cell Probes* 9: 145–156 (1995). In addition, target DNA sequences can be detected by means of the primed in situ labeling technique (PRINS) (Koch et al., *Genet. Anal. Tech. Appl.* 8: 171–8, (1991)). The sensitivity of the detection can be increased by using chemical amplification procedures, e.g., by using tyramide (Speel et al., *J. Histochem. Cytochem.* 45:1439–46, (1997)).

The term "paired hybridization signals" or a "hybridization signal pair" refers to a spatial pattern of hybridization signals wherein two signals are consistently identified in close proximity. Isochromosomes are typically characterized by the presence of "paired hybridization signals" from a single probe. For example, in a sample with many cells, a "hybridization signal pair" is a consistent occurrence of two signals in close proximity that is clearly not due to an artifact or a random event.

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189–197. Other synthetic backbones encompasses by the term include methyl-phosphonate linkages or alternating methylphosphonate and phosphodiester linkages (Strauss-Soukup (1997) *Biochemistry* 36: 8692–8698), and benzylphosphonate linkages (Sainstag (1996) *Antisense Nucleic Acid Drug Dev* 6:153–156). The term nucleic acid is used interchangeably with gene, cDNA, mRNA, oligonucleotide primer, probe and amplification product.

The term a "nucleic acid array" as used herein is a plurality of target elements, each target element comprising one or more nucleic acid molecules (probes) immobilized on one or more solid surfaces to which sample nucleic acids can be hybridized. The nucleic acids of a target element can contain sequence(s) from specific genes or clones, e.g. from specific regions of chromosome 11p or 11q. Other target elements will contain, for instance, reference sequences. Target elements of various dimensions can be used in the arrays of the invention. Generally, smaller, target elements are preferred. Typically, a target element will be less than about 1 cm in diameter. Generally element sizes are from 1 μm to about 3 mm, preferably between about 5 μm and about 1 mm. The target elements of the arrays may be arranged on the solid surface at different densities. The target element densities will depend upon a number of factors, such as the nature of the label, the solid support, and the like. One of skill will recognize that each target element may comprise a mixture of nucleic acids of different lengths and sequences. Thus, for example, a target element may contain more than one copy of a cloned piece of DNA, and each copy may be broken into fragments of different lengths. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The terms "nucleic acid sample" or "sample of human nucleic acid" as used herein refers to a sample comprising human DNA or RNA in a form suitable for detection by hybridization or amplification. Typically, it will be prepared from a skin tissue sample of a tumor from a patient who has or is suspected of having a melanocytic tumor that may be difficult to classify.

The nucleic acid sample can often be a tissue or cell sample prepared for standard in situ hybridization methods described below. The sample is prepared using standard techniques such that individual chromosomes remain substantially intact. Alternatively, the nucleic acid may be isolated, cloned or amplified. It can be, e.g., genomic DNA, mRNA, or cDNA or selected H-RAS sequences (e.g. the promoter, particular exons, or subsequences of the gene, etc.).

The nucleic acid sample is typically extracted from particular cells, e.g. melanocytes, or prepared from a skin tumor, i.e., a melanocytic neoplasm. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from extracts or supernatants from the cells or the cells themselves from cell cultures, cells from tissue culture and other media in which it may be desirable to detect chromosomal abnormalities, such as changes in copy number, isochromosomes, or H-RAS gene mutations. In some cases, the nucleic acids may be amplified using standard techniques such as PCR, prior to the hybridization. The sample may be isolated nucleic acids immobilized on a solid.

The term "probe" or "nucleic acid probe", as used herein, is defined to be a collection of one or more nucleic acid fragments whose hybridization to a sample can be detected. The probe may be unlabeled or labeled as described below so that its binding to the target or sample can be detected. The probe is produced from a source of nucleic acids from one or more particular (preselected) portions of a chromosome, e.g., one or more clones, an isolated whole chromosome or chromosome fragment, or a collection of polymerase chain reaction (PCR) amplification products. The probes of the present invention are produced from nucleic acids found in the regions described herein. The probe or genomic nucleic acid sample may be processed in some manner, e.g., by blocking or removal of repetitive nucleic acids or enrichment with unique nucleic acids. The word "sample" may be used herein to refer not only to detected nucleic acids, but to the detectable nucleic acids in the form in which they are applied to the target, e.g., with the blocking nucleic acids, etc. The blocking nucleic acid may also be referred to separately.

A probe that is "adjacent to the centromere" refers to a probe that hybridize to regions adjacent to the centromere bind to sequences at 11p11.1 to 11p11.2 or 11q11.1 to 11q11.2.

An "11p chromosome arm" is defined cytogeneticallya s encompassing the chromosome from band 11p11 to 11pter.

What "probe" refers to specifically is clear from the context in which the word is used. The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) *Science* 767–773; Johnston (1998) *Curr. Biol.* 8: R171–R174; Schummer (1997) *Biotechniques* 23: 1087–1092; Kern (1997) *Biotechniques* 23: 120–124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background, more typically more than 10 to 100 times background, and do not substantially bind in a significant amount to other proteins present in the sample. Specific binding to an antibody under such conditions may require an antibody that is selected for its specificity for a particular H-RAS protein. For example, an antibody that selectively binds to a polypeptide encoded by a mutated H-RAS gene binds to mutated, but not normal H-RAS.

"Providing a nucleic acid sample" means to obtain a biological sample for use in the methods described in this invention. Most often, this will be done by removing a sample of cells from an animal, but can also be accomplished by using previously isolated cells (e.g. isolated by another person).

"Tissue biopsy" refers to the removal of a biological sample for diagnostic analysis. In a patient with cancer, tissue may be removed from a tumor, allowing the analysis of cells within the tumor.

DESCRIPTION OF THE SPECIFIC EMBODIMENTS

Introduction

Figure 1:
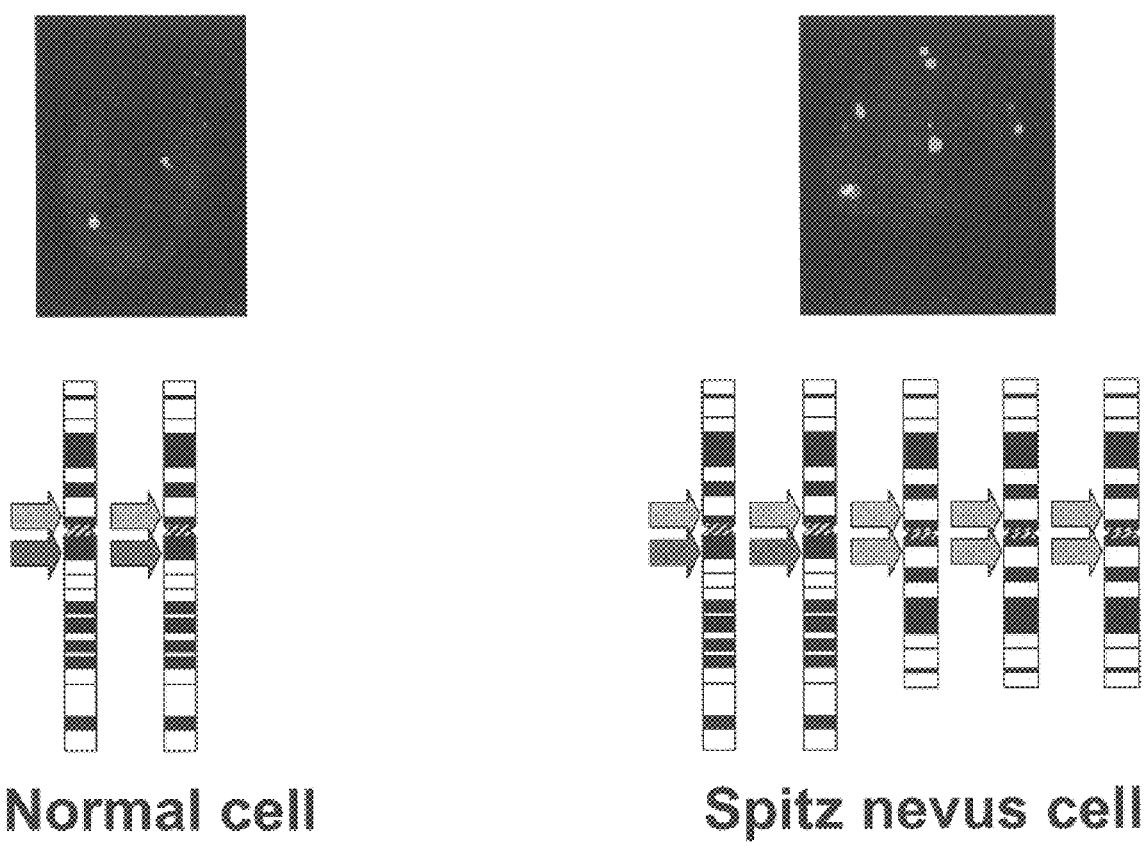
FIG. 1 shows the detection of an 11p isochromosome in a Spitz nevus. One of the red signals is not visible in the focal plane used for the image of the Spitz nevus cell.

The present invention provides methods typing a melanocytic neoplasm by detecting in a skin tumor sample the presence of a mutated H-RAS gene that is associated with the diagnosis of a Spitz nevus. The invention additionally includes methods of identifying the presence of an increased copy number of the 11p chromosome arm, particularly identifying an 11p isochromosome, in a melanocytic neoplasm sample, the presence of which is associated with classification of the neoplasm as a Spitz nevus.

There have been several studies of ploidy in Spitz nevi using measurement of nuclear DNA content by image cytometry or flow cytometry (Howat et al., *Cancer* 63, 474-8 (1989); LeBoit et al., *J Invest Dermatol* 88, 753-7 (1987); Otsuka et al., *Clin Exp Dermatol* 18, 421-4 (1993); Vogt et al., *Am J Dermatopathol* 18, 142–50 (1996)). However, routine application of these techniques has been hampered by the complexity of the procedure and its lack of sensitivity. Recently, molecular cyotgenetic analysis has shown that Spitz nevi, particularly a subset of Spitz nevi, exhibit amplification of chromosome 11p (see, e.g., Bastian et al.,*J. Invest. Dermatol.* 113:1065–1069, 1999; and Bastian et al., *Cancer Res.* 58:2170–2175, 1998), including the 11p15.5 region. As disclosed herein, amplification and/or mutations of the H-RAS gene, which is localized to 11p15.5, are also present in Spitz nevi. As H-RAS is rarely mutated in melanoma (see, e.g., Jiveskog et al., *J. Invest. Dermatol.* 111:757–761, 1998; van Elsas et al., *Am J Pathol.* 149:883–893, 1996), but is mutated in Spitz nevi, mutations in H-RAS can be used to further distinguish a Spitz nevus from melanoma. Accordingly, the present invention provides methods for determining the presence of an amplified H-RAS gene and/or a mutation in an H-RAS gene in a melanocytic neoplasm in order to determine if the neoplasm is a Spitz nevus.

It has been determined that a subset of Spitz nevi recur following excision. The subset typically is characterized by an amplification of the entire 11p chromosome arm, in particular, by the presence of an 11p isochromosome. Amplification of the entire arm of chromosome 11 p has not been observed in melanoma. Thus, the present invention also provides methods of typing or classifying a melanocytic neoplasm as a Spitz nevus by detecting the presence of an increase in copy number of the entire arm of 11p, in particular detecting the presence of an 11p isochromosome.

General Methods of Measuring Chromosomal Abnormality

Genomic instability is a hallmark of solid tumors, and virtually no solid tumor exists which does not show major alterations of the genome. With the vast majority of tumors this instability is expressed at the level of the chromosomal complement, and thus is detectable by cytogenetic approaches (Mitelman, F., Catalog of Chromosome Aberrations in Cancer, 5th Edition (New York: Wiley-Liss) (1994)). However, aneuploidy or chromosomal rearrangement per se is not indicative of malignancy and many benign tumors can have an aberrant karyotype (Mitelman, 1994). To efficiently take advantage of chromosomal abnormalities as a marker, it is mandatory to know characteristic aberrations of the tumors that are to be differentiated.

Several techniques that permit the study of chromosomal complement in post-fixation tissue have been developed. Fluorescence in-situ hybridization (FISH) can be used to study copy numbers of individual genetic loci in interphase nuclei (Pinkel et al., *Proc. Natl. Acad. Sci. U.S.A.* 85, 9138–42 (1988)) and comparative genomic hybridization (CGH) (Kallioniemi et al. *Science* 258, 818–2 1 (1992)) has proven a useful technique (Houldsworth et al. *Am J Pathol* 145, 1253–60 (1994)) to probe for copy number changes of chromosomal regions.

The application of FISH as an adjunctive diagnostic technique for the differentiation of Spitz nevi from melanomas has been suggested previously (De Wit et al., *J Pathol.* 173, 227–33 (1994)). The investigators used a centromeric probe for chromosome 1 and found a significant difference in the number of cells with an aberrant number of signals between 15 melanoma and 15 Spitz nevi. At the time of these earlier studies, no detailed knowledge about chromosomal changes in primary melanomas of the skin was available and chromosome 1 was selected based on its frequent numerical change in melanoma metastasis (Thompson et al., *Cancer Genet Cytogenet* 83, 93–104 (1995)). Chromosomal markers of regions that are frequently involved in chromosomal aberrations present in primary melanomas and those associated with melanocytic neoplasms that are difficult to distinguish from melanoma, e.g., Spitz nevu, are now being developed and thereby permit the use of FISH as a routine method to assist in the differential diagnosis of melanoma and Spitz nevus.

Detection of Mutations in H-RAS

The H-RAS gene is located at 11p15.5, a region which has been shown to be amplified in a subset of Spitz nevi. (Bastian et al., *J. Invest. Dernatol.* 113, 1065–1069, 1999 and co-pending U.S. Ser. No. 09/288,940). Melanocytic neoplasms that are to be typed can be analyzed for the presence of an amplified H-RAS gene as described and further, may be analyzed for the presence of additional mutations in the H-RAS gene. Oncogenic mutations of H-RAS typically involve codons 12, 13, and 61. However, other mutations such as point mutations occurring at any region within the structural gene or regulatory regions of H-RAS, insertions, and deletions can also be detected using the methods of the invention.

There are many methods known in the art for detecting mutations in a given gene. Useful techniques include, but are not limited to, FISH, direct DNA sequencing, Southern blot analysis, single stranded conformation analysis (SSCP), denaturing gradient gel electrophoresis, RNAse protection assays, allele-specific oligonucleotides (ASO), dot blot analysis, PCR-SSCP, and allele-specific PCR.

Another method known in the art is CFLP-cleavase fragment length polymorphism. This method involves amplifying the gene of interest, here H-RAS, followed by digestion with cleavase I, which cuts the DNA at sites dependent on secondary structure. Results are resolved on agarose gels and different patterns of cleavage digestion products are obtained for wild-type and mutant samples.

A further method known in the art is temperature modulation heteroduplex chromatography (TMHC). The method involves amplification of the H-RAS gene followed by denaturing of the PCR products and then slowly cooling, to a predetermined temperature based on the composition of the sample. While cooling, the PCR products renature to form hetero- and homoduplexes which are resolved from one another using TMHC. The resolution can be performed using a WAVE® DNA fragment analysis system (Transgenomic,Inc., San Jose, Calif.).

Mutations in the gene can be found directly by amplifying the gene, e.g., using PCR, in a biological sample, such as a skin tumor sample, and sequencing the amplified product. Alternatively, a probe that specifically hybridizes to the H-RAS gene can used to detect the presence of mutations. Further, a probe that specifically hybridizes to a mutated H-RAS gene, but not the normal gene, e.g., an allele-specific oligonucleotide, can be used to determine the presence of a specific mutation. A probe such as an allele-specific oligonucleotide may be used directly as a probe or as a primer in an amplification reaction in which a product is obtained only if the mutation is present.

Mutations in the H-RAS gene can be detected by a variety of hybridization analyses, which are discussed in further detail below. Detection of single base mutations can be conveniently accomplished by differential hybridization techniques using allele-specific oligonucleotides (see, e.g., Suggs et al., *Proc. Natl. Acad. Sci.* 78: 6613–6617 (1981); Conner et al., *Proc. Natl. Acad. Sci.* 80: 278–282 (1983); Saiki et al., *Proc. Natl. Acad. Sci.* 86: 6230–6234 (1989)). Mutations can be diagnosed on the basis of the higher thermal stability of the perfectly matched probes as compared to the mismatched probes. The hybridization reactions can, for example, be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

An alternative strategy involves detection mutations in the H-RAS gene by sandwich hybridization methods. In this strategy, the mutant and normal target nucleic acids are separated from non-homologous DNA/RNA using a common capture oligonucleotide immobilized on a solid support and detected by specific oligonucleotide probes tagged with reporter labels. The capture oligonucleotides can be immobilized on microtitre plate wells or on beads (Gingeras et al., *J. Infect. Dis.* 164: 1066–1074 (1991); Richman et al., *Proc. Natl. Acad. Sci.* 88: 11241–11245 (1991)).

In one set of embodiments, the hybridizations are performed on a solid support. For example, probes that selectively hybridize to specific mutated H-RAS alleles can be spotted onto a surface. Conveniently, the spots are placed in an ordered pattern, or array, and the placement of the probes on the array is recorded to facilitate later correlation of results. The nucleic acid samples are then hybridized to the array. Conversely, the sample nucleic acids can be spotted onto the surface to form an array and subsequently hybridized to the probes. In one configuration, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606–614; Jackson (1996) *Nature Biotechnology* 14:1685; Chee (1995) *Science* 274: 610; WO 96/17958.

Arrays, particularly nucleic acid arrays can be produced according to a wide variety of methods well known to those of skill in the art (see, e.g., U.S. Pat. No. 6,040,138). For example, in a simple embodiment, "low density" arrays can simply be produced by spotting (e.g. by hand using a pipette) different nucleic acids at different locations on a solid support (e.g. a glass surface, a membrane, etc.).

This simple spotting approach has been automated to produce high density spotted arrays (see, e.g., U.S. Pat. No. : 5,807,522). This patent describes the use of an automated systems that taps a microcapillary against a surface to deposit a small volume of a biological sample. The process is repeated to generate high density arrays. Arrays can also be produced using oligonucleotide synthesis technology. Thus, for example, U.S. Pat. No. 5,143,854 and PCT patent publication Nos. WO 90/15070 and 92/10092 teach the use of light-directed combinatorial synthesis of high density oligonucleotide arrays.

In various embodiments, the array nucleic acids are derived from previously known sequences. For example, arrays can include probes to detect particular mutations in the H-RAS gene. The arrays can be hybridized with a single population of sample nucleic acid or can be used with two differentially labeled collections (as with an test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

Target elements of various sizes, ranging from 1 mm diameter down to 1 $\mu$m can be used. Smaller target elements containing low amounts of concentrated, fixed probe DNA are used for high complexity comparative hybridizations since the total amount of sample available for binding to each target element will be limited. Thus it is advantageous to have small array target elements that contain a small amount of concentrated probe DNA so that the signal that is obtained is highly localized and bright. Such small array target elements are typically used in arrays with densities greater than $10^4/cm^2$. Relatively simple approaches capable of quantitative fluorescent imaging of 1 $cm^2$ areas have been described that permit acquisition of data from a large number of target elements in a single image (see, e.g., Wittrup, *Cytometry* 16: 206–213, 1994).

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques (described above). Nucleic acids can be conveniently coupled to glass using commercially available reagents. For instance, materials for preparation of silanized glass with a number of functional groups are commercially available or can be prepared using standard techniques (see, e.g., Gait (1984) Oligonucleotide Synthesis: A Practical Approach, IRL Press, Wash., D.C.). Quartz cover slips, which have at least 10-fold lower autofluorescence than glass, can also be silanized.

Alternatively, the samples can be placed in separate wells or chambers and hybridized in their respective well or chambers. The art has developed robotic equipment permitting the automated delivery of reagents to separate reaction chambers, including "chip" and microfluidic techniques, which allow the amount of the reagents used per reaction to be sharply reduced. Chip and microfluidic techniques are taught in, for example, U.S. Pat. No. 5,800,690, Orchid, "Running on Parallel Lines" New Scientist, Oct. 25, 1997, McCormick, et al., *Anal. Chem.* 69:2626–30 (1997), and Turgeon, "The Lab of the Future on CD-ROM?" *Medical Laboratory Management Report*. Dec. 1997, p.1. Automated hybridizations on chips or in a microfluidic environment are contemplated methods of practicing the invention.

Although microfluidic environments are one embodiment of the invention, they are not the only defined spaces suitable for performing hybridizations in a fluid environment. Other such spaces include standard laboratory equipment, such as the wells of microtiter plates, Petri dishes, centrifuge tubes, or the like can be used.

The above techniques can be used to locate single base mutations. Typically, the analyses or performed using an amplified region of the H-RAS gene. For example, the gene can be amplified exon by exon, by intron, or at the exon-intron borders. Specific primers, e.g., for amplifying exons 1 and 2, are set forth in the Examples. A multitude of other primers could, however, be generated from the sequence of the genomic DNA, following the teachings of Ausubel in *Current Protocols in Molecular Biology* (Ausubel et al., eds., 1994), and other standard references. Additionally, methods directed to detection of mRNA transcripts, such as reverse-transcriptase PCR (see, e.g., Ausubel, supra).

Amplification-based Assays

In another embodiment, amplification-based assays can be used to detect mutations. In such amplification-based assays, the nucleic acid sequences act as a template in an amplification reaction (e.g., PCR). In a quantitative amplification, the amount of amplification product will be proportional to the amount of template in the original sample. Comparison to appropriate (e.g. healthy tissue) controls provides a measure of the copy number of the desired target nucleic acid sequence. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.).

Other suitable amplification methods include, but are not limited to ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), and self-sustained sequence replication (Guatelli et al. (1990) *Proc. Nat. Acad. Sci. USA* 87: 1874).

Detection of Isochromosomes

Changes in copy number of a particular gene or chromosomal region can be due to a number of mechanisms, including the presence of an isochromosome, in which one of the arms of a chromosome is duplicated, thus increasing the copy number of the sequences located on the duplicated arm. Methods of evaluating the copy number of a particular gene or chromosomal region, and particularly analyzing for the presence of an isochromosome, are well known to those of skill in the art. An increase in copy number of the whole arm of chromosome 11 can be detected, e.g., using procedures described in co-pending application U.S. Ser. No. 09/288,940 now U.S. Pat. No. 6,261,775. Copy number changes, and particularly, isochromosomes, are typically detected using hybridzation-based assays, such as FISH.

The presence of an isochromosome can be detected using a single probe to that hybridizes to a region on the duplicated chromosomal arm. Typically, the probe will be localized to a regions of the chromosomal arm that is adjacent to the centromere. Normal cells have two randomly positioned signals in their nucleus. Cells that possess an isochromosome will have one to several pairs of signals present in the nucleus.

Preferably, an isochromosome is detected using two probes, each labeled with a distinct compound, e.g., different fluorescent labels with distinguishable colors. Usually, the analysis employs two probes that hybridize to nucleic acid sequences close to the centromere. One of the probes hybridizes to target sequences on the p arm that are adjacent to the centromere, e.g., sequences localized to 11p11.1 or 11p1.2. The second probe hybridizes to target sequences on the q arm adjacent to the centromer, i.e., 11q11.1 or 11q11.2. An isochromosome is detected by determining the presence of hybridization regions that occur as pairs of the same color compared to a normal situation in which the visualized pairs contain two colors.

Hybridization-based Assays

In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. The preferred size range is from about 200 bp to about 1000 bases, more preferably between about 400 to about 800 bp for double stranded, nick translated nucleic acids.

In some applications it is necessary to block the hybridization capacity of repetitive sequences. Thus, in some embodiments, human genomic DNA or Cot-1 DNA is used to block non-specific hybridization.

In Comparative Genomic Hybridization (CGH) methods a first collection of (sample) nucleic acids (e.g. from a possible tumor) is labeled with a first label, while a second collection of (control) nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number.

Hybridization protocols suitable for use with the methods of the invention are described, e.g., in Albertson (1984) *EMBO J*. 3: 1227–1234; Pinkel (1988) *Proc. Natl. Acad. Sci. USA* 85: 9138–9142; EPO Pub. No. 430,402; *Methods in Molecular Biology*, Vol. 33: *In Situ Hybridization Protocols*, Choo, ed., Humana Press, Totowa, N.J. (1994), etc. In one particularly preferred embodiment, the hybridization protocol of Pinkel et al. (1998) *Nature Genetics* 20:207–211 or of Kallioniemi (1992) *Proc. Natl Acad Sci USA* 89:5321–5325 (1992) is used.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.1 to about 0.5 mg/ml DNA (e.g., cot-1 DNA). The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology*, Vol. 24: *Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background membranes can be used (see, e.g., Chu (1992) *Electrophoresis* 13:105–114). The sensitivity for detection of spots ("target elements") of various diameters on the candidate membranes can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., membranes, glass, fused silica) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

Labeling and Detection of Nucleic Acids

In a preferred embodiment, the hybridized nucleic acids are detected by detecting one or more labels attached to the sample or probe nucleic acids. The labels may be incorporated by any of a number of means well known to those of skill in the art. Means of attaching labels to nucleic acids include, for example nick translation or end-labeling (e.g. with a labeled RNA) by kinasing of the nucleic acid and subsequent attachment (ligation) of a nucleic acid linker joining the sample nucleic acid to a label (e.g., a fluorophore). A wide variety of linkers for the attachment of labels to nucleic acids are also known. In addition, intercalating dyes and fluorescent nucleotides can also be used.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence. Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. The nucleic acid probe may also be labeled with digoxigenin and then detected with an antibody that is labeled with a fluorochrom, or an enzyme such as horseradish peroxidase or alkaline phosphatase. For a detailed review of methods of labeling nucleic acids and detecting labeled hybridized nucleic acids see *Laboratory Techniques in Biochemistry and Molecular Biology*, Vol. 24: *Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science*, 281: 2013–2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016–2018).

Detection of Gene Expression

The amount of H-RAS present in a sample can be detected by, for instance, measuring levels of the gene transcript (e.g. mRNA), or by measuring the quantity of translated protein.

Detection of Gene Transcripts

Methods of detecting and/or quantifying gene transcripts using nucleic acid hybridization techniques are known to those of skill in the art (see Sambrook et al. supra) and include Northern blotting and RT-PCR. For example, RT-PCR may be used for for directly assessing copy number of the H-RAS target sequences. Furthermore, any number of quantitative techniques are available, such as Taqman (Perkin-Elmer), that enable the real-time detection of the amount of H-RAS transcript in a sample.

Detection of Expressed Protein

The presence of H-RAS can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like. For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991).

Immunoassays can be performed in any of several configurations, which are reviewed extensively in Enzyme Immunoassay (Maggio, ed., 1980); and Harlow & Lane, supra. Immunoassays also often use a labeling agent to specifically bind to and label the complex formed by the antibody and antigen. The labeling agent may itself be one of the moieties comprising the antibody/antigen complex. Thus, the labeling agent may be a labeled H-RAS polypeptide or a labeled anti-H-RAS antibody. Alternatively, the labeling agent may be a third moiety, such a secondary antibody, that specifically binds to the antibody/H-RAS complex (a secondary antibody is typically specific to antibodies of the species from which the first antibody is derived). Other proteins capable of specifically binding immunoglobulin constant regions, such as protein A or protein G, may also be used as the label agent. These proteins exhibit a strong nonimmunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Immunoassays for detecting H-RAS in a sample may be either competitive or noncompetitive. Noncompetitive immunoassays are assays in which the amount of antigen is directly measured. In one preferred "sandwich" assay, for example, the anti-H-RAS antibodies can be bound directly to a solid substrate on which they are immobilized. These immobilized antibodies then capture the H-RAS protein present in the test sample. The H-RAS thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

In competitive assays, the amount of H-RAS protein present in the sample is measured indirectly by measuring the amount of a known, added (exogenous) H-RAS protein displaced (competed away) from an anti-H-RAS antibody by the unknown H-RAS protein present in a sample. In one competitive assay, a known amount of H-RAS protein is added to a sample and the sample is then contacted with an antibody that specifically binds to the H-RAS protein. The amount of exogenous H-RAS protein bound to the antibody is inversely proportional to the concentration of H-RAS protein present in the sample. In a particularly preferred embodiment, the antibody is immobilized on a solid substrate. The amount of H-RAS bound to the antibody may be determined either by measuring the amount of H-RAS present in a H-RAS/antibody complex, or alternatively by measuring the amount of remaining uncomplexed protein. The amount of H-RAS may be detected by providing a labeled H-RAS molecule.

A hapten inhibition assay is another preferred competitive assay. In this assay, the known H-RAS protein is immobilized on a solid substrate. A known amount of anti-H-RAS antibody is added to the sample, and the sample is then contacted with the immobilized H-RAS. The amount of anti-H-RAS antibody bound to the known immobilized H-RAS protein is inversely proportional to the amount of H-RAS present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Western blot (immunoblot) analysis is used to detect and quantify the presence of H-RAS in a sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind H-RAS, and/or antibodies that specifically bind to mutated H-RAS proteins. The anti-H-RAS polypeptide antibodies specifically bind to the H-RAS polypeptide on the solid support. These antibodies may be directly labeled or alternatively may be subsequently detected using labeled antibodies (e.g., labeled sheep anti-mouse antibodies) that specifically bind to the anti-H-RAS antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Kits for Use in Diagnostic and/or Prognostic Applications.

For use in diagnostic, research ,and therapeutic applications suggested above, kits are also provided by the invention. In the diagnostic and research applications such kits may include any or all of the following: assay reagents, buffers, nucleic acids for detecting the target sequences and other hybridization probes and/or primers. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Example One
Identification of H-RAS Mutations

This example demonstrates that a mutated H-RAS gene is associated with Spitz nevus. The procedures to identify H-RAS mutations were performed following standard protocols as described as follows.

Selection of cases: Paraffin blocks of Spitz nevi were retrieved randomly from the archives of the Dermatopathology section of the Departments of Dermatology and Pathology at the University of California, San Francisco. We performed a computer search of the database of the Dermatopathology Section with the following criteria: select all cases from Jan. 1, 1998 to Dec. 31, 1998 that were assigned a main diagnosis of one 30 different descriptive variants of Spitz nevus that are used in our laboratory. Cases sent in as a slide in consultation were excluded in order to avoid a bias towards unusual Spitz nevi. The request yielded 144 cases from which blocks were available.

In addition to these cases, 22 cases of the Department of Dermatology University of Würzburg, Germany were included in the study. These cases had originally been retrieved for comparative genomic hybridization and only included Spitz nevi with at least 1 mm thickness.

Assembly of tissue arrays: Tissue arrays were constructed according to Kononen et. al., (Nat. Med. 4:844–847, 1998). In brief, a tissue arraying instrument (Beecher Instruments, Silver Spring, Md.) was used to punch 0.8 mm biopsy cores of the most cellular areas of the nevi. The biopsy cores were arrayed in recipient paraffin blocks, according to the manufacturer's instructions. Multiple sections of 6 $\mu$m thickness were cut with a microtome using an adhesive-coated tape sectioning system (Instrumedics, Hackensack, N.J.). H&E sections were used for the histological examination of the biopsy cores. Only cases with at least one area with a cohesive population of neoplastic melanocytes were included in the analysis.

FISH to formalin-fixed tissue microarray sections: Dual-color FISH was carried out on tissue sections of the array as described previously (Bastian et al., *J. Invest. Dermatol.* 113:1065–1069, 1999). We used a BAC clone (RMC11B022) that contained H-RAS for the detection of amplifications of chromosome 11p, and a reference P1 clone (RMC11P008) for the q-arm of chromosome 11. Probes were labeled with Cy3 (Amersham, Arlington Heights, Ill.) or with digoxigenin (Boehringer Mannheim, Indianapolis Ind.) by nick-translation. Tissue sections were deparaffinized, hydrated, and pre-treated for 2–4 min in 1M sodium thiocyanate at 80° C., in 4 mg/ml Pepsin in 0.2 N HCl at 37° C. for 4–8 min. After dehydration, sections were denatured in 70% formamide, 2×SSC pH 7.0 for 5 min at 72° C., and hybridized over 48–72 h at 37° C. in 10 $\mu$l hybridization buffer (50% formamide, 10% dextran sulfate, and 2×SSC, pH 7.0, 20 $\mu$g Cot-1 DNA (Life Technologies, Inc., Gaithersburg, Md.)). Slides were washed three times in washing solution (50% formamide in 2×SSC, pH 7.0) at 45° C., once in 2×SSC at 45° C., once in 2×SSC at room temperature (RT), and once in 0.1% TritonX100 in 4×SSC/ at RT. Subsequently, sections were incubated with 10% BSA in 4×SSC in a moist chamber at 37° C., and then with a FITC labeled anti-digoxigenin antibody (Boehringer Mannheim, Indianapolis Ind.) diluted in 4×SSC with 10% BSA. Sections were counterstained with 4,6-diamino-2-phenylindole (Sigma, St. Louis, Mo.) in an anti-fade solution. FISH signals were scored with a fluorescence microscope Zeiss (Jena, Germany) using a 63X objective. Criteria for amplification were: at least three times more test probe signals than reference signals in at least 30% of the tumor cells.

DNA Sequence Analysis: DNA was extracted from 30 $\mu$m sections from which the tumor-bearing areas were dissected manually with a scalpel under a dissecting microscope. Two to three sections were collected in a 0.5 ml tube and after washing with xylene and ethanol were incubated at 55° C. with 0.4 mg/ml proteinase K (Life Technologies, Inc., Gaithersburg, Md.) in PCR buffer (Perkin Elmer) containing 0.5% Tween 20 for three days. Fresh proteinase K was added every 24h to a final concentration of 0.4 mg/ml. HRAS codon 12 primers were 5'-AGGAGACCCTGTAGGAGGA-3' (SEQ ID NO: 1) (forward) and 5'-CGCTAGGCTCACCTCTATAGTG-3' (SEQ ID NO:2) (reverse) and codon 61 primers were 5'-CTGCAGGATTCCTACCGGA-3' (SEQ ID NO:3) and 5'-ACTTGGTGTTGTTGATGGCA-3' (SEQ ID NO:4). PCR was carried out in a Gene Amp PCR System 9700 Thermal Cycler (Perkin Elmer) in 25 $\mu$l reaction volumes. Each PCR reaction contained 3.5 mM $MgCl_2$, 0.2 mM dNTP, 0.625 U Taq Gold Polymerase (Perkin Elmer), 1X PCR Buffer II, 0.5 $\mu$M each of forward and reverse primer, and 50–300 ng of genomic DNA. PCR cycling conditions were as follows: 95° C. for 15 min followed by 35 cycles of 95° C. for 15 sec, 55° C. for 30 seconds, and 72° C. for 60 seconds, and a final hold at 72° C. for 10 minutes.

Prior to sequencing, PCR products were purified using the PCR product Pre-sequencing kit (Amersham, Arlington Heights, Ill.) to remove excess primers and nucleotides. Fluorescent DNA sequencing was carried out using Big Dye terminator sequencing chemistry (PE Applied Biosystems). Briefly, 30–50 ng of purified PCR product and 3.2 pmol of sequencing primer were used for sequencing in a 15 $\mu$l reaction according to the manufacturer's instructions. The sequencing products were purified using a Sephadex G50 column, dried in a vacuum concentrator and resuspended in 3 $\mu$l of gel loading buffer (83% deionized formamide, 17% gel loading dye) (PE Applied Biosystems). 0.5 $\mu$l of the sample was then loaded on a denaturing sequence gel on an ABI automated DNA sequencer. All samples were sequenced in both forward and reverse directions to confirm the presence/absence of mutations. The data were analyzed using the Sequencher software (Gene Codes, Ann Arbor, Mich.).

FISH Analysis of Chromosome 11p Copy Number Using Tissue Arrays

High-quality hybridizations of cases in which tumor cells could be definitively identified were obtained from 102 cases. This yield of 61.4% is relatively low compared to arrays that we have constructed from melanomas. Most of the cases that could not be analyzed were very small Spitz nevi that consisted only of single cells or small nests of junctional melanocytes so that the neoplastic melanocytes could not be reliably recognized in the array. Thirty nine cases (38.2%) were from male and 61 (59.8%) from female patients, in two cases the gender was not known. The mean age was 30.0 years. 52 (51%) of the cases had features of the pigmented spindle cell nevus variant of Spitz (PSCN).

The hybridization efficiency could be assessed by counting the hybridization signals in normal epidermis that was present in many of the biopsies. The average copy numbers for test and reference probes in normal keratinocytes were 1.7 and 1.6, respectively. Hybridizations were analyzed of three separate sections of the array, and counts from two or more sections were available for 47 (46.1 %) cases. In 45 (95.7%) of these, the result of the separate counts were identical, in one case a definitive amplification was seen in one analysis, and was not found in the cells present in the other section. Amplifications were only scored if more than 30% of the tumor cells had at least 3-fold increased signals of 11p when compared to the reference probe on 11q. According to these criteria, amplification of 11p was found in 12 (11.8%) cases. The average thickness of cases with amplifications was significantly greater than the thickness of cases with normal copy number of 11p (1.1 mm vs. 0.6 mm, p=0.01). The amplification frequency within the randomly retrieved set of cases was 6/84 (7.1 %), whereas of the 18 cases that had been selected for thickness, 6 (33.3%) showed amplifications of chromosome 11p.

H-RAS mutations

Oncogenic mutations of H-RAS typically involve codons 12, 13 in exon 1 and codon 61 in exon 2 (Barbacid, M., Annu. Rev. Biochem: 56:779–827, 1987). We sequenced exons 1 and 2 of H-RAS of 9 cases in which FISH detected an amplification of chromosome 11p, and in 13 cases in which FISH showed normal copy numbers of chromosome 11p. Five of nine cases (56%) with 11p amplification had HRAS mutations, significantly more (p=0.002) than in the cases with normal 11p copy numbers, in which only one (8%) had a mutation. Three mutations were 61Gln->Leu, two 61 Gln->Arg, and one 12 Gly->Arg.

Additionally, we sequenced H-RAS in 11 Spitz nevi used for our previous CGH analysis (Bastian et al., J. Invest. Dermatol. 113:1065–1069, 1999). H-RAS mutations were identified in all three cases (100%) in which CGH detected increased copies of chromosome 11p. All of these involved codon 61; two cases had a transition of glutamine to arginine, and the other to leucine. The seven cases in which CGH found normal copy numbers of chromosome 11p had wild-type sequences of both exons of H-RAS.

Of the total of 33 Spitz nevi in which H-RAS was sequenced, 8/12 cases (67%) with amplified 11p had H-RAS mutations, significantly more (p<0.0001) than in the cases with normal copies of chromosome 11p (1/21 or 5%).

Histologic Features of Cases with Amplified Chromosome 11p

Amplifications were most common in compound or predominantly intradermal Spitz nevi (11/47 or 23.4%), and only rarely occurred in the pigmented spindle cell variant of Spitz nevus (1/52 or 1.9%; p=0.0007). The cases with amplification of 11p frequently showed several histological features that occurred infrequently in the cases with normal copy number of chromosome 11p (Table 1). The tumors commonly showed single cells splayed between collagen bundles at the base resulting in a pattern of haphazardly arranged collagen and marked desmoplasia (8/12, p=0.0005). Cells typically had vesicular nuclei with delicate nuclear membranes, and ample amphophilic cytoplasm. Cells at the base frequently (5/12) seemed to be surrounded by thin, eosinophilic membranes), that were only seen in 3 of the 87 cases that had normal copy numbers of 11p (p<0.0001). These membranes stained positive with a reticulin stain (not shown). Cases with 11p amplifications were also notably more pleomorphic (p<0.0001) with nuclei varying in sizes and shapes and staining intensity and in some cases intranuclear inclusions. These features were also present in the three cases that had shown amplification of chromosome 11p by comparative genomic hybridization in a previous study (Bastian et al., J. Invest. Dermatol. 113:1065–1069, 1999). No association of 11p amplification with patient age or sex was found.

TABLE 1

Histological features associated with amplification of chromosome 11p in Spitz nevi.

| Histology | n | 11p amplified | 11p normal | p-Value |
|---|---|---|---|---|
| Desmoplasia | 26 (25.5%) | 8 (30.8%) | 18 (69.2%) | 0.000552 |
| Eosinophilic membranes | 8 (7.8%) | 5 (62.5%) | 3 (37.5%) | 0.000004 |
| Single cells between collagen bundles | 23 (22.5%) | 5 (21.7%) | 12 (52.2%) | 0.014305 |
| Marked nuclear pleomorphism | 30 (29.4%) | 10 (33.3%) | 20 (66.7%) | 0.000015 |

The percentages in the n column refer to the total number of 102 cases. The other percentages refer to the number of cases that have the respective biological feature.

Cell proliferation using a Ki-67 antibody was assessed in all 12 cases with amplifications of 11p and 24 cases with normal copy numbers of chromosome 11p. Immunostains were performed on sections of the original blocks to allow inspection of sufficient numbers of cells. In 11/12 (92%) of the cases with 11p amplification and 20/24 (83%) with normal 11p copy numbers the number of labeled nuclei ranged from 0 to maximal 1%. A total of five cases had higher labeling rates: Four had normal 11p copy numbers and a labeling index of at most 5%, mostly affecting melanocytes at the demo-epidermal junction. One case that had an average of 6 copies of chromosome 11p by FISH analysis and a 61G->A mutation had a labeling index of 10%. It was a superficial biopsy, so that the proliferation rate in deeper areas of the nevus could not be assessed.

Overexpression of $\alpha_v\beta_3$ Integrin in Spitz nevi with 11p Amplification The expression of the cellular adhesion molecule $\alpha_v\beta P_3$ integrin is correlated with tumor progression and invasion in melanoma (Albelda et al., Cancer Res. 1990, 50:6757–6764) and has recently been reported to be expressed in Spitz nevus (Van Belle et al., Hum. Pathol. 1999, 30:562–567). The pattern of single cells between collagen bundles leading to a considerable remodelling of collagen frequently found in cases with 11p amplification was indicative of a marked invasive capacity of the cells. Immunohistochemistry to detect β3 integrin was performed to determine the level of $\alpha_v\beta_3$ integrin expression. This analysis showed that of a total of 80 informative cases, 29 (41.4%) showed expression (1+ and above) of $\alpha_v\beta_3$ integrin. $\alpha_v\beta_3$ integrin expression was significantly (p<0.0001) associated with amplification of HRAS. Of 29 cases which expressed $\alpha_v\beta_3$ integrin, 9 had amplifications of HRAS. Of 41 cases without expression of $\alpha_v\beta_3$ integrin, only two cases had an amplification of chromosome 11p. In all cases with 11p amplification the expression pattern of $\alpha_v\beta_3$ integrin was membranous.

In summary, this example shows that H-RAS mutations are present in a subset of Spitz nevus and can be used as a target in typing tumor samples to assist in the differential diagnosis of a Spitz nevus.

Example Two

Identification of 11p Isochromosomes

Ten Spitz nevi samples that showed amplification of H-RAS (see, e.g., Example 1) were analyzed for the presence of an 11p isochromosome using FISH. A representative experiment is depicted in FIG. 1.

Two probes were employed for the analysis. The first probe RPCI-1156c13, which was labeled with FITC and detected as a green fluorescent signal, maps to chromosome 11p to a region adjacent to the centromere, 11p11.2. The second probe RPCI-11135h08, which was labeled with Cy3 and detected as a red fluorescent label, hybridizes to sequences on the q arm of chromosome 11 adjacent to the centromere at 11q11. Normal control tissue showed only the presence of paired hybridization signals containing two colors, i.e., the pair of signals included one red signal and one green signal. The results from all of the 10 samples from Spitz nevi indicated the additional presence of paired hybridization signals of the same color (green). These results demonstrate the presence of an 11p isochromosome.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Sequence Listing:

SEQ ID NO: 1 HRAS codon 12 forward primer
5'-AGGAGACCCTGTAGGAGGA-3'

SEQ ID NO: 2 HRAS codon 12 reverse primer
5'-CGCTAGGCTCACCTCTATAGTG-3'

SEQ ID NO:3 HRAS codon 61 forward primer
5'-CTGCAGGATTCCTACCGGA-3'

SEQ ID NO:4 HRAS codon 61 reverse primer
5'-ACTTGGTGTTGTTGATGGCA-3'

What is claimed is:

1. A method of typing a Spitz nevus in a skin tumor sample from a patient, the method comprising:
   a) detecting an increase in copy number of H-Ras in the skin tumor sample compared to normal
   b) detecting the presence or absence of a mutation at codon 12 or codon 61 in H-Ras wherein the presence of a mutation at codon 12 or codon 61 of H-Ras in a sample with an increase in copy number of H-Ras is indicative of Spitz nevi.

2. The method of claim 1, wherein the step of detecting the presence or absence of a mutation comprises
   amplifying a nucleic acid that encodes H-RAS or a fragment thereof;
   sequencing the amplified product; and
   determining the presence of the mutation in the amplified product.

3. The method of claim 2, wherein the amplifying step comprises a PCR reaction.

4. The method of claim 3, wherein the primers for the PCR reaction are SEQ ID NOs: 1 and 2.

5. The method of claim 3, wherein the primers for the PCR reaction are SEQ ID NOs: 3 and 4.

6. The method of claim 2, wherein the nucleic acid is genomic DNA.

7. The method of claim 2, wherein the nucleic acid is RNA.

8. The method of claim 1, wherein the step of detecting the presence or absence of a mutation comprises
   contacting a nucleic acid from the sample with a probe that selectively hybridizes to the mutation in the mutant H-RAS target nucleic acid sequence to form a stable hybridization complex, wherein the nucleic acid is contacted with the probe under conditions in which the probe binds selectively to the mutant H-RAS target nucleic acid sequence.

9. The method of claim 8, wherein the nucleic acid is amplified in an amplifying step.

10. The method of claim 8, wherein the amplifying step comprises a PCR reaction.

11. The method of claim 8, wherein the nucleic acid is genomic DNA.

12. The method of claim 8, wherein the nucleic acid is RNA.

13. A method of typing a Spitz nevus in a skin tumor sample from a patient, the method comprising detecting the presence of an 11p isochromosome, thereby typing the Spitz nevus.

14. The method of claim 13, wherein the detecting step comprises:
   hybridizing a nucleic acid from the sample with a first probe labeled with a detectable label, wherein the probe selectively hybridizes to a target nucleic acid sequence on chromosome 11p adjacent to the centromere, and
   detecting the presence of paired hybridization signals from the first probe.

15. The method of claim 14, wherein the detecting step further comprises hybridizing the nucleic acid from the sample with a second probe labeled with a second detectable label distinguishable from the first, wherein the second probe selectively hybridizes to a target nucleic acid sequence on chromosome 11q adjacent to the centromere; and further comprising detecting a signal from the second label that is next to the signal from the first.

16. The method of claim 15, wherein the first label is a fluorescent label and the second label is a fluorescent label that is a different color from the first.

* * * * *

```
                       SEQUENCE LISTING

<160> NUMBER OF SEQ ID NOS:   4

<210> SEQ ID NO 1
    <211> LENGTH: 19
    <212> TYPE: DNA
    <213> ORGANISM: Artificial Sequence
    <220> FEATURE:
    <223> OTHER INFORMATION: Description of Artificial Sequence:HRAS codon
          12 forward primer

<400> SEQUENCE: 1
aggagaccct gtaggagga                                                   19

<210> SEQ ID NO 2
    <211> LENGTH: 22
    <212> TYPE: DNA
    <213> ORGANISM: Artificial Sequence
    <220> FEATURE:
    <223> OTHER INFORMATION: Description of Artificial Sequence:HRAS codon
          12 reverse primer

<400> SEQUENCE: 2
cgctaggctc acctctatag tg                                               22

<210> SEQ ID NO 3
    <211> LENGTH: 19
    <212> TYPE: DNA
    <213> ORGANISM: Artificial Sequence
    <220> FEATURE:
    <223> OTHER INFORMATION: Description of Artificial Sequence:HRAS codon
          61 forward primer

<400> SEQUENCE: 3
ctgcaggatt cctaccgga                                                   19

<210> SEQ ID NO 4
    <211> LENGTH: 20
    <212> TYPE: DNA
    <213> ORGANISM: Artificial Sequence
    <220> FEATURE:
    <223> OTHER INFORMATION: Description of Artificial Sequence:HRAS codon
          61 reverse primer

<400> SEQUENCE: 4
acttggtgtt gttgatggca                                                  20
```